US011219611B2

(12) United States Patent
Wang et al.

(10) Patent No.: US 11,219,611 B2
(45) Date of Patent: *Jan. 11, 2022

(54) FORMULATIONS OF L-ORNITHINE PHENYLACETATE

(71) Applicant: Ocera Therapeutics, Inc., Palo Alto, CA (US)

(72) Inventors: Laurene Wang, Chapel Hill, NC (US); Stanley Bukofzer, Chicago, IL (US); Linda S. Grais, San Francisco, CA (US)

(73) Assignee: Ocera Therapeutics, Inc., Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,910

(22) Filed: Nov. 11, 2016

(65) Prior Publication Data

US 2017/0135973 A1 May 18, 2017

Related U.S. Application Data

(63) Continuation-in-part of application No. 15/133,087, filed on Apr. 19, 2016.

(60) Provisional application No. 62/276,754, filed on Jan. 8, 2016, provisional application No. 62/255,300, filed on Nov. 13, 2015.

(51) Int. Cl.
| | | |
|---|---|---|
| *A61K 31/198* | (2006.01) | |
| *A61K 9/00* | (2006.01) | |
| *A61K 9/08* | (2006.01) | |
| *A61K 9/50* | (2006.01) | |
| *A61K 31/222* | (2006.01) | |

(52) U.S. Cl.
CPC .......... *A61K 31/198* (2013.01); *A61K 9/0053* (2013.01); *A61K 9/08* (2013.01); *A61K 9/5026* (2013.01); *A61K 9/5047* (2013.01); *A61K 9/5078* (2013.01); *A61K 31/222* (2013.01)

(58) Field of Classification Search
CPC .. A61K 9/0053; A61K 9/5026; A61K 9/5047; A61K 9/5089; A61K 31/198; A61K 31/222

See application file for complete search history.

(56) References Cited

U.S. PATENT DOCUMENTS

| | | | |
|---|---|---|---|
| 4,228,099 A | 10/1980 | Walser | |
| 5,741,524 A | 4/1998 | Staniforth et al. | |
| 5,767,086 A | 6/1998 | Kauvar et al. | |
| 8,173,706 B2 * | 5/2012 | Anderson | A61P 43/00 514/576 |
| 9,566,257 B2 | 2/2017 | Jalan et al. | |
| 10,525,029 B2 | 1/2020 | Jalan et al. | |
| 10,550,069 B2 | 2/2020 | Anderson et al. | |
| 10,610,506 B2 | 4/2020 | Jalan et al. | |
| 2003/0105104 A1 | 6/2003 | Burzynski | |
| 2004/0229948 A1 | 11/2004 | Summar et al. | |
| 2005/0182064 A1 | 8/2005 | Burzynski | |
| 2008/0119554 A1 | 5/2008 | Jalan et al. | |
| 2008/0206324 A1 | 8/2008 | Gryczke et al. | |
| 2010/0280119 A1 | 11/2010 | Jalan et al. | |
| 2012/0157526 A1 * | 6/2012 | Jalan | A61K 31/19 514/555 |
| 2012/0208885 A1 | 8/2012 | Anderson et al. | |
| 2012/0259016 A1 | 10/2012 | Jalan et al. | |
| 2013/0211135 A1 | 8/2013 | Anderson et al. | |
| 2013/0296429 A1 | 11/2013 | Anderson et al. | |
| 2014/0288327 A1 | 9/2014 | Anderson et al. | |
| 2015/0133684 A1 | 5/2015 | Anderson et al. | |
| 2015/0251990 A1 | 9/2015 | Anderson et al. | |
| 2016/0338982 A1 | 11/2016 | Ruettimann et al. | |
| 2017/0189364 A1 | 7/2017 | Jalan et al. | |

FOREIGN PATENT DOCUMENTS

| | | |
|---|---|---|
| AU | 2014250643 A1 | 11/2014 |
| AU | 2015221466 A1 | 9/2015 |
| CN | 1383815 | 12/2002 |
| CN | 101626769 A | 1/2010 |
| CN | 103705490 A | 4/2014 |
| JP | 2008-521784 | 6/2008 |
| JP | S54-163518 | 12/2011 |
| WO | WO 1987/05297 | 9/1987 |
| WO | WO 2003/045372 | 6/2003 |

(Continued)

OTHER PUBLICATIONS

Bosoi, C.R. et al., "Long Term Oral Treatment of Ornithine Phenylacetate Increases Lean Mass and Attenuates Brain Edema in Bile-duct Ligated Rats", Hepatol. (Oct. 2015) 62(Suppl 1):953A [Abs. 1523].
Lukkarinen M. et al., "Effect of Lysine Infusion on Urea Cycle in Lysinuric Protein Intolerance", Metabol. (2000) 49(5):621-625.
International Search Report and Written Opinion dated Jan. 27, 2017 for Application No. PCT/US2016/061678, filed Nov. 11, 2016.
Batshaw et al., "Alternative pathway therapy for urea cycle disorders: twenty years later," J. Pediatr. (2001) 138 (1 Suppl): S46-S55.
Berge et al., Review Article: Pharmaceutical Salts, J Pharm Sci, 1977, vol. 66, pp. 1-19.
Briggs et al., Effect of Ornithine and Lactate on Urea Synthesis in Isolated Hepatocytes, Biochem J, 1976, vol. 160, pp. 205-209.

(Continued)

*Primary Examiner* — Michael B. Pallay
(74) *Attorney, Agent, or Firm* — Knobbe, Martens, Olson & Bear, LLP

(57) ABSTRACT

Some embodiments of the present application are directed to oral formulations of L-ornithine phenylacetate and methods of using the same. These oral formulations offer alternative administration route than the standard intravenous administration of L-ornithine phenylacetate for treating hyperammonemia in patients having various acute and chronic liver diseases and disorders, for example, acute liver failure, liver cirrhosis, liver decompensation, portal hypertension, hepatic encephalopathy, or patients with urea cycle disorders.

28 Claims, 4 Drawing Sheets

(56) References Cited

FOREIGN PATENT DOCUMENTS

| WO | WO 2006/056794 A1 | 6/2006 |
|---|---|---|
| WO | WO 2010/115055 A1 | 10/2010 |
| WO | WO 2010/144498 A1 | 12/2010 |
| WO | WO 2012/048043 A1 | 4/2012 |
| WO | WO 2016/172112 A1 | 10/2016 |

OTHER PUBLICATIONS

Database WPI, Section Ch, Week 200331, Derwent Publications Ltd., London, GB; XP002364873 & CN 1383815 A (Liu W), Dec. 11, 2002 (Abstract Only).
Greenstein et al., Studies on the Metabolism of Amino Acids and Related Compounds in Vivo. III. Prevention of Ammonia Toxicity by Arginine and Related Compounds, Arch Biochem Biophys, 1956, vol. 64, Issue (2):, pp. 342-354.
Häberle et al., Hyperammonämie: Ursachen, Diagnostik, Therapie, Dtsch Med Wochenschr, 2004, vol. 129; pp. 1430-1433.
Iyer et al., "Mouse model for human arginase deficiency", Mol Cell Biol., 2002, vol. 22, Issue 13, pp. 4491-4498.
Jalan et al., "Acute-on-chronic liver failure: pathophysiological basis of therapeutic options", Blood Purif, 2002, vol. 20, pp. 252-261.
Jalan et al., "Moderate hypothermia in patients with acute liver failure and uncontrolled intracranial hypertension,", Gastroenterology, 2004, vol. 5, Issue 127, pp. 1338-1346.
Jalan et al., "The molecular pathogenesis of hepatic encephalopathy", The International Journal of Biochemistry & Cell Biology, 2003, vol. 35, pp. 1175-1181.
Jalan et al., L-Ornithine Phenylacetate (OP): A Novel Treatment for Hyperammonemia and Hepatic Encephalopathy, Medical Hypotheses (2007) 69(5): 1064-1069, Elsevier Ltd.
Jalan et al., Treatment of Hyperammonemia in Liver Failure: A Tale of Two Enzymes, Gastroenterology, 2009, p. 2048-2051, vol. 1236.
Jalan,, Intracranial Hypertension in Acute Liver Failure: Pathophysiological Basis of Rational Management, Seminars in Liver Disease, 2003, p. 271-282, vol. 23, No. 3, Thieme Medical Publishers, Inc., New York, NY, USA.
Jover-Cobos et al., Ornithine phenylacetate revisited; Metabolic Brain Disease (2013) 28(2): 327-331.
Lukkarinen, M. et al., Oral Supplementation Corrects Plasma Lysine Concentrations in Lysinuric Protein Intolerance, Metabolism, Jul. 2003, vol. 52, No. 7, pp. 935-938.
Mendenhall et al., "A new therapy for portal systemic encephalopathy", The American Journal of Gastroenterology, 1986, vol. 81, Issue 7, pp. 540-543.
Mouille et al., Adaptative increase of ornithine production and decrease of ammonia metabolism in rat colonocytes after hyperproteic diet ingestion, Am J Gastrointest Liver Physiol., 2004, vol. 287, pp. 344-351.
Ocera Therapeutics, Inc., News Release: Ocera Completes Interim Analysis of OCR-002 in Phase 2b STOP-HE Study for the Treatment of Acute Hepatic Encephalopathy; Globe Newswire; Apr. 1, 2015, 2 pages.
Ocera Therapeutics, Inc., News Release: Ocera Announces Positive Phase 1 Results for Oral OCR-002 in Development for the Prevention of Acute Hepatic Encephalopathy; Globe Newswire; Nov. 16, 2015, 2 pages.
Ocera Therapeutics, Inc., News Release: Ocera Completes Plasma Data from Pilot Phase 1 Study for Orally-available OCR-002 in Development for the Prevention of Acute Hepatic Encephalopathy; Globe Newswire; Jan. 8, 2016, 3 pages.
Riordan et al., "Treatment of hepatic encephalopathy", Curr Concepts, 1997, vol. 337, Issue 7, pp. 473-479.
Rockey et al., "Randomized, Double-Blind, Controlled Study of Glycerol Phenylbutyrate in Hepatic Encephalopathy," Hepatology, 2014, 59(3): 1073-1083.
Rogers et al., Deficiency of Pyrroline-5-Carboxylate Synthase in the Intestinal Mucosa of the Cat, The Journal of Nutrition, 1985, pp. 146-150, vol. 115, No. 1, American Institution of Nutrition.
Stedman's Medical Dictionary; "Encephalopathy", 27th Edition (2002); 1 page.
Stewart, P. M., et al., Effects of Arginine-Free Meals on Ureagenesis in Cats, American Journal of Physiological, 1981, pp. E310-E315, vol. 241, No. 4, The American Physiological Society.
Suchy et al., Clinical Manifestations and Complications—Typical Clinical Presentation;, Liver Disease in Children, 2nd Edition, 2001, pp. 74-77.
Tuchman, M., et al., Management of Inherited Disorders of Ureagenesis, The Endocrinologist, 2002, vol. 12, No. 2, p. 99-109.
Ventura-Cots et al., Safety of ornithine phenylacetate in cirrhotic decompensated patients: an open-label, dose-escalating, single-cohort study; J Clin Gastroenter. (2013) 47(10): 881-887.
International Search Report and Written Opinion dated May 30, 2016 in Application No. PCT/US2016/028298, filed Apr. 19, 2016.
Mokhtaran et al., *"Urinary Phenylacetylglutamine as Dosing Biomarker for Patients with Urea Cycle Disorders"*, Mol Genet Metab. 2012; 107(3): 308-314.
OCERA Therapeutics, Inc., News Release: Ocera Initiates Phase 1 Clinical Trial of Oral Drug Candidate OCR-002 for Prevention of Hepatic Encephalopathy; Globe Newswire; Sep. 16, 2015, 4 pages.
New Zealand Examination Report dated Aug. 31, 2018 for corresponding Application No. 741658, filed Apr. 16, 2018.
Balasubramaniyan et al., "Ammonia reduction with ornithine phenylacetate restores brain eNOS activity via the DDAH-ADMA pathway in bile duct-ligated cirrhotic rats", Am J Physiol Gastrointest Liver Physiol., (published online Sep. 8, 2011) 2012, 302(1):G145-152.
Hyperion Therapeutics, Inc., Ravicti™ (glycerol phenylbutyrate) Oral Liquid—Highlights of Prescribing Information; Jan. 2013 in 23 pages.
Kristiansen et al., "L-Ornithine phenylacetate reduces ammonia in pigs with acute liver failure through phenylacetylglycine formation: a novel ammonia-lowering pathway", Am J Physiol Gastrointest Liver Physiol., 2014, 307(10):G1024-1031.
Alekseyev et al., "Excipients in the technology of modified-release tablets", Collective of Authors, Pharmacy, 2009, vol. 6, pp. 49-56.
Canbay et al. "L-Ornithine L-Aspartate (LOLA) as a Novel Approach for Therapy of Nonalcoholic Fatty Liver Disease", Drugs 2019, vol. 79(Suppl 1), pp. S39-S44 (first published online Jan. 31, 2019).
Wan et al., "L-ornithine phenylacetate, a new medicine to treat hepatic encephalopathy", Chinese J New Drugs, 2013, 22(11):1274-1277.
Ytreb Ø et al., "L-Ornithine Phenylacetate Attenuates Increased Arterial and Extracellular Brain Ammonia and Prevents Intracranial Hypertension in Pigs with Acute Liver Failure", Hepatology, Jul. 2009, 50(1): 165-174.
European Extended Search Report dated Jun. 5, 2019 for Application No. 16865158.6.
Ahuja et al., "Direct acting inhibitors of ammoniagenesis: A role in post-TIPS encephalopathy?", Annals of Hepatology, 2014, 13(2): 179-186.

* cited by examiner

FORMULATIONS OF L-ORNITHINE PHENYLACETATE

INCORPORATION BY REFERENCE TO PRIORITY APPLICATIONS

The present application claims the benefit of priority to U.S. Provisional Patent Application No. 62/255,300, filed Nov. 13, 2015; U.S. Provisional Patent Application No. 62/276,754, filed Jan. 8, 2016; and U.S. application Ser. No. 15/133,087, filed Apr. 19, 2016; all which are hereby expressly incorporated by reference in their entireties.

BACKGROUND

Field

The present application relates to pharmaceutical compositions comprising oral formulations of L-ornithine phenylacetate and methods of administration and the use for treating hyperammonemia in patients having various acute and chronic liver diseases and disorders, for example, acute liver failure, liver cirrhosis, liver decompensation, portal hypertension, hepatic encephalopathy, or patients with urea cycle disorders.

Description

Chronic liver disease is characterized by the gradual destruction of liver tissue over time, whereby healthy and regenerating liver tissue is slowly replaced with scar and necrotic tissue. This is known as liver cirrhosis. Normal liver function is impaired and the scar tissue progressively diminishes blood flow through the liver. As normal regenerating liver tissue is lost, nutrients, hormones, drugs and toxins are no longer effectively processed. This can result in symptoms including abnormal clearance of proteins absorbed through the intestinal tract, leading to accumulation of ammonia; abnormal excretion, leading to an accumulation of bilirubin in the blood, producing jaundice; increased sinusoidal pressure, leading to fluid accumulation in the abdomen (ascites); and portal hypertension (and portosystemic shunting) wherein scarred liver tissue acts as a barrier to blood flow, leading to increased portal blood pressure and oesophageal varices.

Patients with chronic liver disease can be in a fairly stable clinical state and exhibit few or no symptoms. However, such patients are at risk of an abrupt deterioration in their condition which can lead to acute-on-chronic liver failure. This transition from a "compensated" state, where the liver is able to function, albeit at a reduced level, to a "decompensated" state, where liver function fails, involves the effect of precipitating events. Precipitating events associated with chronic liver disease include gastrointestinal bleeding, infection (sepsis), portal vein thrombosis and dehydration.

Hepatic encephalopathy (HE) is a common complication of decompensated cirrhosis; it has a significant negative effect on survival even after liver transplantation and is associated with irreversible impairment in cognitive function. An estimated 60-70% of cirrhotic subjects have at least subtle signs of neurocognitive impairment, and HE is the principal diagnosis in hospitalized subjects. Overt HE has a prevalence of approximately 30% in the cirrhotic population, and accounts for about 150,000 hospitalizations annually in the United States.

Hepatic encephalopathy (HE) is a complex neuropsychiatric disorder that occurs in diverse clinical situations such as acute or chronic liver disease and spontaneous portosystemic venous shunting. In the early stages of hepatic encephalopathy subtle mental changes occur such as poor concentration, confusion and disorientation. In severe cases, hepatic encephalopathy can lead to stupor, coma, brain swelling (cerebral edema) and death. In the case of patients who develop HE as a result of chronic liver disease, the onset of HE is often the result of a clinically precipitating event such as gastrointestinal bleeding, sepsis (infection), portal vein thrombosis or dehydration.

Gastrointestinal bleeding and portosystemic shunting allows toxic substances, which are usually metabolized by the liver, to bypass the liver, enter the systemic circulation and cross the blood-brain barrier to exert direct or indirect neurotoxic effects on the central nervous system. Ammonia accumulation is thought to play an important role in the progression of hepatic encephalopathy and multiorgan failure (respiratory failure, cardiovascular failure, kidney failure). In addition to ammonia, septicaemia (or bacterial peritonitis) which develops soon after a gastrointestinal bleed is also likely to be a contributing factor to hepatic encephalopathy.

Liver decompensation can then lead to multi-organ failure and hepatic encephalopathy. In the early stages of hepatic encephalopathy subtle mental changes such as poor concentration or the inability to construct simple objects occurs. In severe cases, hepatic encephalopathy can lead to stupor, coma, brain swelling and death.

Urea cycle disorder or urea cycle defect is a genetic disorder caused by a deficiency of one of the enzymes in the urea cycle which is responsible for removing ammonia from the blood stream. Normally, the urea is transferred into the urine and removed from the body. In urea cycle disorders, the nitrogen accumulates in the form of ammonia, a toxic substance, and is not removed from the body. It has been reported that sodium phenylbutyrate may be used in the management of this condition. See, for example, Batshaw, M. L. et al., "Alternative pathway therapy for urea cycle disorders: twenty years later," J. Pediatr. (2001) 138 (1 Suppl): S46-S55.

A common therapy for patients with hepatic encephalopathy involves strategies to reduce the concentration of ammonia. These include restriction of dietary protein intake; administration of lactulose, neomycin, L-ornithine L-aspartate (LOLA), or sodium benzoate; and cleansing enemas. There are currently marketed products that contain phenylacetic acid (e.g., AMMONUL®) or prodrugs of phenylacetic acid, e.g., phenylbutyrate (BUPHENYL®) or glycerol phenylbutyrate (RAVICTI®) as the ammonia scavenger (binding agent) for the treatment of hyperammonemia due to urea cycle disorder (UCDs). RAVICTI® has also been evaluated in clinical trials and shown preliminary efficacy for the treatment of hepatic encephalopathy. See, for example, Rockey D. et al., "Randomized, Double-Blind, Controlled Study of Glycerol Phenylbutyrate in Hepatic Encephalopathy," Hepatology, 2014, 59(3):1073-1083. In addition, L-ornithine phenylacetate has been reported to be an effective treatment of hyperammonemia and hepatic encephalopathy. Jalan et al., reported a clinical study where the data showed that L-ornithine phenylacetate is useful in ammonia lowering. See Jalan et al., "L-Ornithine phenylacetate (OP): a novel treatment for hyperammonemia and hepatic encephalopathy," Med Hypotheses 2007; 69(5): 1064-69. See also, U.S. Publication Nos. 2008/0119554, 2010/0280119, and 2013/0211135, each of such is hereby incorporated by reference in its entirety.

L-ornithine phenylacetate has been granted orphan drug status by the United States Food and Drug Administration and was granted fast track designation for the treatment of hyperammonemia and resultant hepatic encephalopathy. Currently, L-ornithine phenylacetate is under clinical investigation for the treatment of overt HE in patients with decompensated liver cirrhosis. Patients receive continuous intravenous infusion of L-ornithine phenylacetate at doses of 10, 15 or 20 g per day for 5 days depending on the baseline severity of the liver impairment.

Typically, L-ornithine phenylacetate has excellent solubility in water or aqueous solution. In all the known clinical studies of L-ornithine phenylacetate for treating acute or chronic liver diseases, L-ornithine phenylacetate is administered by intravenous infusion over a period of time, for example, from 1 day or up to five days in human studies. There exists a need to develop alternative administration routes to improve patient convenience.

SUMMARY

Some embodiments of the present disclosure relate to oral pharmaceutical formulations, comprising L-ornithine phenylacetate in an oral dosage of about 0.1 g to about 10 g, and one or more pharmaceutically acceptable excipients or carriers. In some embodiments, the formulation provides an immediate release profile of L-ornithine phenylacetate upon oral administration. In some embodiment, the oral dosage of L-ornithine phenylacetate is from about 2 g to about 8 g. In one embodiment, the oral dosage of L-ornithine phenylacetate is about 5 g. In another embodiment, the oral dosage of L-ornithine phenylacetate is about 2.5 g. In some other embodiment, the oral pharmaceutical formulation provides controlled release of L-ornithine phenylacetate.

Some embodiments of the present disclosure relate to methods of treating or ameliorating hyperammonemia comprising administering to a subject in need thereof an oral pharmaceutical formulation comprising L-ornithine phenylacetate as described herein. In some embodiments, the subject has acute liver failure or chronic liver diseases. In some embodiments, the subject has liver cirrhosis or liver decompensation. In some embodiments, the subject has hepatic encephalopathy. In still some embodiments, the subject has portal hypertension. In some further embodiments, the chronic liver disease or liver cirrhosis is classified as Child-Pugh A, B or C.

Some embodiments of the present disclosure relate to methods of treating hyperammonemia comprising administering to a subject in need thereof an oral pharmaceutical formulation comprising L-ornithine phenylacetate, where the pharmaceutical formulation provides a plasma Cmax of phenylacetic acid ranging from about 10 µg/mL to about 150 µg/mL. In some embodiments, the pharmaceutical formulation also provides a plasma Cmax of phenylacetylglutamine ranging from about 5 µg/mL to about 100 µg/mL. In some embodiments, the oral pharmaceutical formulation of L-ornithine phenylacetate provides a controlled release of L-ornithine phenylacetate after administration. In some other embodiments, the oral pharmaceutical formulation of L-ornithine phenylacetate provides an immediate release of L-ornithine phenylacetate after administration. In some embodiments, the pharmaceutical formulation comprise L-ornithine phenylacetate in an oral dosage of about 0.1 g to about 10 g.

DETAILED DESCRIPTION OF THE EMBODIMENTS

Figure 1:
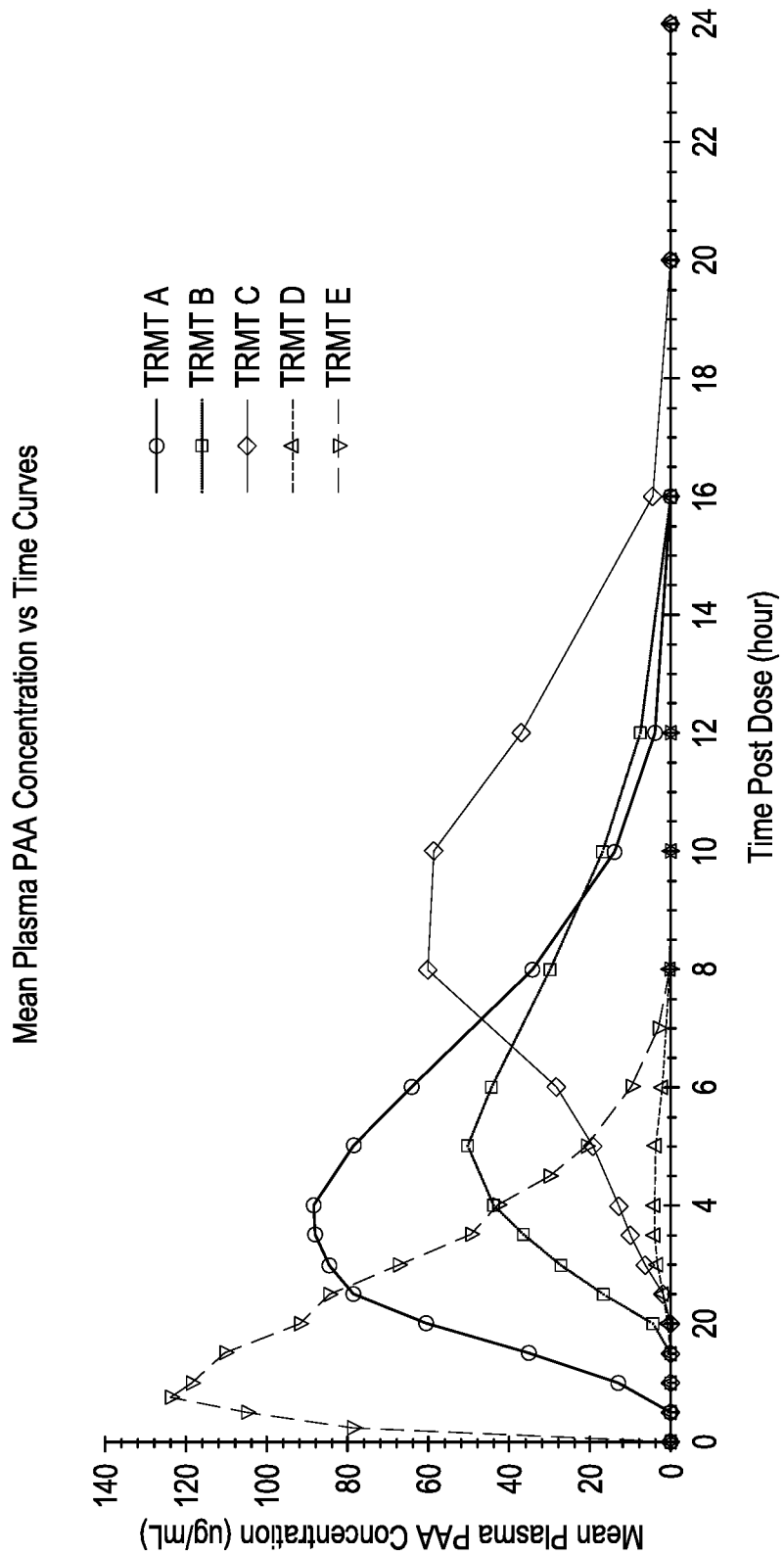
FIG. 1 is a line chart depicting the in vivo plasma pharmacokinetic profiles of phenylacetic acid (PAA) in humans after administration of controlled-release Formulations A, B, and C, RAVICTI®, and an immediate-release oral formulation of L-ornithine phenylacetate.

Some embodiments of the present disclosure are directed to oral formulations of L-ornithine phenylacetate. Some embodiments of the formulations provide a low dose formulation, using much lower doses of equivalent phenylacetate as compared to RAVICTI®. Some such embodiments are an immediate release formulation. Other embodiments of the formulations provide a controlled release or extended release system.

Definitions

The section headings used herein are for organizational purposes only and are not to be construed as limiting the subject matter described.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, formulation, or device, the term "comprising" means that the compound, composition, formulation, or device includes at least the recited features or components, but may also include additional features or components.

As used herein, common organic abbreviations are defined as follows:

AUC Area under the curve $AUC_{0-t}$ Area under the concentration vs. time curve from time=0 (zero) to time of last quantifiable concentration $AUC_{0-inf}$ Area under the plasma concentration with time curve extrapolated to infinite time CL Total plasma clearance $C_{12}$ Drug concentration at 12 hr after drug administration Cmax Maximum plasma concentration F Absolute bioavailability value (%)

hr Hour(s)

IR Immediate release

ORN Ornithine

PAA Phenylacetic acid (or the conjugate base phenylacetate)

PAGN Phenylacetylglutamine

PD Pharmacodynamic

PK Pharmacokinetic

The term "immediate release" as used herein, has its ordinary meaning as understood by those skilled in the art and thus includes, by way of non-limiting example, release of a drug from a dosage form in a relatively brief period of time after administration.

The term "controlled release" and the term "extended release" as used herein, each has its ordinary meaning as understood by those skilled in the art and thus includes, by way of non-limiting example, controlled release of a drug from a dosage form over an extended period of time. For example, in some embodiments, controlled release or extended release formulations are those that have a release rate that is substantially longer than that of a comparable immediate release form. The two terms can be used interchangeably.

The term "about" as used herein, refers to a quantity, value, number, percentage, amount, or weight that varies from the reference quantity, value, number, percentage, amount, or weight by a variance considered acceptable by one of ordinary skill in the art for that type of quantity, value, number, percentage, amount, or weight. In various embodiments, the term "about" refers to a variance of 20, 15, 10, 9, 8, 7, 6, 5, 4, 3, 2 or 1% relative to the reference quantity, value, number, percentage, amount, or weight.

The term "oral dosage form" as used herein, has its ordinary meaning as understood by those skilled in the art and thus includes, by way of non-limiting examples, a formulation of a drug or drugs in a form orally administrable to a human, including pills, tablets, cores, capsules, caplets, loose powder, liquid solution or suspension.

The term "phenylacetic acid" as used herein, is also known as benzeneacetic acid or 2-phenylacetic acid). It has the following chemical structure:

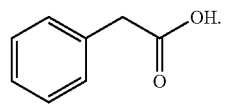

The term "phenylacetate" as used herein, refers to the anionic form of phenylacetic acid with the following chemical structure:

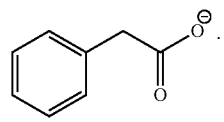

The term "L-ornithine phenylacetate" as used herein, refer to a compound consisting of L-ornithine cation and phenylacetate anion. It has the following chemical structure:

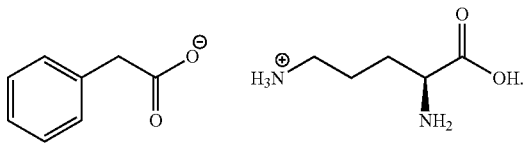 [SMILES: O=C([O-])Cc1ccccc1 ; N[C@@H](CCC[NH3+])C(=O)O]

The term "phenylacetylglutamine" as used herein, refers to the product formed by the conjugation of phenylacetic acid and glutamine. It is a common metabolite that can be found in human urine. It has the following chemical structure:

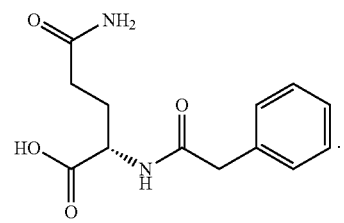 [SMILES: NC(=O)CC[C@H](NC(=O)Cc1ccccc1)C(=O)O]

As used herein, the term "percent conversion of phenylacetate to phenylacetylglutamine over 24 hours" refers to the mass percent of phenylacetate administered to a patient that is converted to phenylacetylglutamine collected over 24 hours in the urine.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions or formulations is contemplated. Supplementary active ingredients can also be incorporated into the compositions or formulations. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

"Treat," "treatment," or "treating," as used herein refers to administering a pharmaceutical composition/formulation for prophylactic and/or therapeutic purposes. The term "prophylactic treatment" refers to treating a patient who is not yet suffering from a disease, but who is susceptible to, or otherwise at risk of, a particular liver disease, whereby the treatment reduces the likelihood that the patient will develop a liver disease. The term "therapeutic treatment" refers to administering treatment to a patient already suffering from a liver disease.

The compositions or formulations described herein are preferably provided in unit dosage form. As used herein, a "unit dosage form" is a composition/formulation containing an amount of a compound that is suitable for administration to an animal, preferably mammal subject, in a single administration, according to good medical practice. The preparation of a single or unit dosage form however, does not imply that the dosage form is administered once per day or once per course of therapy, or that the unit dosage form contains all of the dose to be administered at a single time. Such dosage forms are contemplated to be administered once, twice, thrice or more per day, and may be given more than once during a course of therapy, though a single administration is not specifically excluded. In addition, multiple unit dosage forms may be administered at substantially the same time to achieve the full dose intended (e.g., two or more tablets may be swallowed by the patient to achieve a complete dose). The skilled artisan will recognize that the formulation does not specifically contemplate the entire course of therapy and such decisions are left for those skilled in the art of treatment rather than formulation.

As used herein, the act of "providing" includes supplying, acquiring, or administering (including self-administering) a composition described herein.

As used herein, the term "administering" a drug includes an individual obtaining and taking a drug on their own. For example, in some embodiments, an individual obtains a drug from a pharmacy and self-administers the drug in accordance with the methods provided herein.

In any of the embodiments described herein, methods of treatment can alternatively entail use claims, such as Swiss-type use claims. For example, a method of treating fibrosis with a composition can alternatively entail the use of a composition in the manufacture of a medicament for the treatment of fibrosis, or the use of a composition for the treatment of fibrosis.

Those skilled in the art will understand that pharmacokinetic parameters may be determined by comparison to a reference standard using clinical trial methods known and accepted by those skilled in the art, e.g., as described in the examples set forth herein. Since the pharmacokinetics of a drug can vary from patient to patient, such clinical trials generally involve multiple patients and appropriate statistical analyses of the resulting data (e.g., ANOVA at 90% confidence). Comparisons of pharmacokinetic parameters can be on a dose-adjusted basis, as understood by those skilled in the art.

Low Dose Formulations

Some embodiments of the present disclosure relate to ORAL pharmaceutical formulations, comprising L-ornithine phenylacetate in an dosage of about 0.1 g to about 10 g, and one or more pharmaceutically acceptable excipients or carriers. In some embodiments, the formulation provides an immediate release profile of L-ornithine phenylacetate upon administration (for example, an immediate-release oral formulation in the form of a liquid solution or suspension). Other embodiments provide a controlled-release or extended release profile. In preferred embodiments, the pharmaceutical formulation is an oral pharmaceutical formulation. In some embodiments, the L-ornithine phenylacetate is in a dosage of about 0.5 g, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g, or in a dosage range defined by any of the two preceding values (for example, about 1 g to about 9 g, about 2 g to about 8 g, about 3 g to about 7 g, about 4 g to about 6 g, about 1 g to about 6 g, about 1 g to about 5 g, about 1 g to about 4 g, about 1 g to about 3 g, about 2 g to about 6 g, about 2 g to about 5 g, or about 2 g to about 4 g). In one embodiment, the oral dosage is about 2.5 g. In another embodiment, the oral dosage is about 5 g.

In some embodiments, the pharmaceutical formulation is in a single unit dosage form. In some other embodiments, the pharmaceutical formulation is in two or more unit dosage forms (i.e., a divided dose). For example, where an oral dosage is about 5 g, it may be provided in the form of four or five tablets, each containing about 1.25 g or 1 g of L-ornithine phenylacetate. In some embodiments, the unit dosage form is a tablet, a capsule, a pill, pellets, free-flowing powder, or liquid. In one embodiment, the unit dosage form is a liquid solution comprising 5 g of L-ornithine phenylacetate.

In some embodiments, the pharmaceutical formulation provides conversion of phenylacetate to phenylacetylglutamine over 24 hours of greater than about 30%, greater than about 40%, greater than about 50%, greater than about 60%, greater than about 70%, greater than about 80%, or greater than about 90%. In some further embodiments, the formulation provides conversion of phenylacetate to phenylacetylglutamine over 24 hours of greater than about 80%. In some embodiments, the conversion efficiency is determined based on excreted urinary phenylacetylglutamine.

In some embodiments, the pharmaceutical formulation provides conversion of phenylacetate to phenylacetylglutamine over 12 hours of greater than about 30%, greater than about 40%, greater than about 50%, greater than about 60%, greater than about 70%, greater than about 80%, or greater than about 90%. In some further embodiments, the formulation provides conversion of phenylacetate to phenylacetylglutamine over 12 hours of greater than about 60%. In some embodiments, the conversion efficiency is determined based on excreted urinary phenylacetylglutamine.

The low dose pharmaceutical formulations described herein may be administered by any suitable route, for example, it may be administered by oral, intravenous, intragastric, intraperitoneal or intravasular routes. In a preferred embodiment, the pharmaceutical formulation of L-ornithine is an oral dosage form, for example, a oral solution. In another embodiment, the pharmaceutical formulation is an intravenous dosage form.

Methods of Treatment

Some embodiments of the present disclosure relate to methods of treating or ameliorating hyperammonemia comprising orally administering to a subject in need thereof a pharmaceutical formulation comprising an effective amount of L-ornithine phenylacetate, in particular the oral pharmaceutical formulation as described herein. In some embodiments, the subject has acute liver failure or chronic liver diseases. In some embodiments, the subject has liver cirrhosis or liver decompensation. In some such embodiment, the chronic liver disease or liver cirrhosis has a classification of Child-Pugh class A, B or C. Some embodiments comprise identifying a subject as having a liver disease with a classification of Child-Pugh A and then administering a composition as described herein. Some embodiments comprise identifying a subject as having a liver disease with a classification of Child-Pugh B and then administering a composition as described herein. In some embodiments, the subject has hepatic encephalopathy. Some embodiments comprise identifying a subject as having a liver disease with a classification of Child-Pugh C and then administering a composition as described herein. In still some embodiments, the subject has portal hypertension. In some embodiments, the subject has a urea cycle disorder. In some other embodiment, the subject has recently discontinued treatment of lactulose, for example, the subject has discontinued treatment of lactulose for 1 day, 2 days, 3 days, 4 days, 5 days, 6 days, 1 week, 2 weeks, 3 weeks, 4 weeks, or longer.

In some embodiments of the methods described herein, the methods described herein provide a plasma Cmax of phenylacetic acid ranging from about 10 µg/mL to about 150 µg/mL. In some such embodiments, the plasma Cmax of phenylacetic acid is from about 20 µg/mL to about 140 µg/mL. In some such embodiments, the plasma Cmax of phenylacetic acid is from about 30 µg/mL to about 130 µg/mL. In some such embodiments, the plasma Cmax of phenylacetic acid is from about 40 µg/mL to about 120 µg/mL. In some further embodiments, the plasma Cmax of phenylacetic acid is from about 50 µg/mL to about 110 µg/mL.

In some embodiments of the methods described herein, the plasma Cmax of metabolite phenylacetylglutamine ranges from about 5 µg/mL to about 100 µg/mL. In some such embodiments, the plasma Cmax of metabolite phenylacetylglutamine is from about 10 µg/mL to about 80 µg/mL. In some such embodiments, the plasma Cmax of metabolite phenylacetylglutamine is from about 20 µg/mL to about 60 µg/mL. In some such embodiments, the plasma Cmax of metabolite phenylacetylglutamine is from about 25 µg/mL to about 50 µg/mL. In some further embodiments, the plasma Cmax of metabolite phenylacetylglutamine is from about 30 µg/mL to about 45 µg/mL.

Some embodiments of the present disclosure relate to methods of treating hyperammonemia comprising administering to a subject in need thereof an oral pharmaceutical formulation comprising L-ornithine phenylacetate, where the pharmaceutical formulation provides a plasma Cmax of phenylacetic acid ranging from about 10 µg/mL about 150 µg/mL. In particular, the oral pharmaceutical composition comprising L-ornithine phenylacetate provides a plasma Cmax of phenylacetic acid of about 10 µg/mL, about 15 µg/mL, about 20 µg/mL, about 25 µg/mL, about 30 µg/mL, about 35 µg/mL, about 40 µg/mL, about 45 µg/mL, about 50 µg/mL, about 55 µg/mL, about 60 µg/mL, about 65 µg/mL, about 70 µg/mL, about 75 µg/mL, about 80 µg/mL, about 85 µg/mL, about 90 µg/mL, about 95 µg/mL, about 100 µg/mL, about 105 µg/mL, about 110 µg/mL, about 115 µg/mL, about 120 µg/mL, about 125 µg/mL, about 130 µg/mL, about 135 µg/mL, about 140 µg/mL, about 145 µg/mL, or about 150 µg/mL, or a range as defined by any of the two preceding values. In one embodiment, the plasma Cmax level of phenylacetic acid is from about 20 µg/mL to about 140 µg/mL. In another embodiment, the plasma Cmax level of phenylacetic acid is from about 30 µg/mL to about 130 µg/mL. In still another embodiment, the plasma Cmax level of phenylacetic acid is from about 40 µg/mL to about 120 µg/mL. In a further embodiment, the plasma Cmax level of phenylacetic acid is from about 50 µg/mL to about 110 µg/mL. In some embodiments, the plasma $AUC_{0-t}$ or $AUC_{0-inf}$ of phenylacetic acid is from about 100 to about 1000 hr*µg/mL, from about 150 hr*µg/mL to about 900 hr*µg/mL, from about 200 hr*µg/mL to about 800 hr*µg/mL, from about 250 hr*µg/mL to about 700 hr*µg/mL, from about 300 hr*µg/mL to about 650 hr*µg/mL, from about 350 hr*µg/mL to about 600 hr*µg/mL, or from about 400 hr*µg/mL to about 550 hr*µg/mL. In some embodiments, the pharmaceutical formulation also provides a plasma Cmax of phenylacetylglutamine ranging from about 5 µg/mL to about 100 µg/mL. In particular, the oral pharmaceutical composition comprising L-ornithine phenylacetate provides a plasma Cmax of phenylacetylglutamine of about 5 µg/mL, about 10 µg/mL, about 15 µg/mL, about 20 µg/mL, about 25 µg/mL, about 30 µg/mL, about 35 µg/mL, about 40 µg/mL, about 45 µg/mL, about 50 µg/mL, about 55 µg/mL, about 60 µg/mL, about 65 µg/mL, about 70 µg/mL, about 75 µg/mL, about 80 µg/mL, about 85 µg/mL, about 90 µg/mL, about 95 µg/mL, or about 100 µg/mL, or a range as defined by any of the two preceding values. In one embodiment, the plasma Cmax of phenylacetylglutamine is from about 10 µg/mL to about 80 µg/mL. In another embodiment, the plasma Cmax of phenylacetylglutamine is from about 20 µg/mL to about 60 µg/mL. In yet another embodiment, the plasma Cmax of phenylacetylglutamine is from about 25 µg/mL to about 50 µg/mL. In some embodiments, the plasma $AUC_{0-t}$ of phenylacetylglutamine is from about 25 hr*µg/mL to about 500 hr*µg/mL, from about 50 hr*µg/mL to about 300 hr*µg/mL, from about 100 hr*µg/mL to about 200 hr*µg/mL, or from about 120 hr*µg/mL to about 180 hr*µg/mL. In some embodiments, the plasma $AUC_{0-inf}$ of phenylacetylglutamine is from about 25 hr*µg/mL to about 500 hr*µg/mL, or from about 50 hr*µg/mL to about 400 hr*µg/mL, from about 75 hr*µg/mL to about 300 hr*µg/mL, from about 100 hr*µg/mL to about 250 hr*µg/mL, or from about 150 hr*µg/mL to about 200 hr*µg/mL.

In some embodiments of the methods described herein, the oral pharmaceutical composition is administered under fasting condition. In some other embodiments, the oral pharmaceutical composition is administered under fed condition, for example, concurrently or within 60 minutes after a meal.

In some embodiments of the methods described herein, the oral pharmaceutical formulation of L-ornithine phenylacetate provides a controlled release of L-ornithine phenylacetate after administration. In some other embodiments, the oral pharmaceutical formulation of L-ornithine phenylacetate provides an immediate release of L-ornithine phenylacetate after administration.

In some embodiments of the methods described herein, L-ornithine phenylacetate is administered in an amount from about 0.1 g to about 50 g per day, from about 0.5 g to about 45 g per day, from about 1 g to about 40 g per day, from about 1.5 g to about 35 g per day, from about 2 g to about 30 g per day, from about 2.5 g to about 25 g per day, from about 3 g to about 20 g per day, or from about 5 g to about 15 g per day. In some embodiments, the pharmaceutical formulation is for administration at least once a day. In some further embodiments, the pharmaceutical formulation is for administration two or more times per day. In one embodiment, the pharmaceutical formulation is for thrice daily oral administration.

In some embodiments of the methods described herein, L-ornithine phenylacetate is administered as a single dose in an amount from about 1.0 g to about 10.0 g. In some further embodiments, L-ornithine phenylacetate is administered as a single dose in an amount from about 2 g to about 8 g. In various other embodiments, L-ornithine phenylacetate is administered as a single dose in a range of about 1 g to about 9 g, about 2 g to about 8 g, about 3 g to about 7 g, about 4 g to about 6 g, about 1 g to about 6 g, about 1 g to about 5 g, about 1 g to about 4 g, about 1 g to about 3 g, about 2 g to about 6 g, about 2 g to about 5 g, or about 2 g to about 4 g. In one embodiment, L-ornithine phenylacetate is administered as a single dose in an amount about 2.5 g. In another embodiment, L-ornithine phenylacetate is administered as a single dose in an amount about 5 g. In some such embodiment, the pharmaceutical formulation containing such amount of L-ornithine phenylacetate is in a single oral dosage form. In some other such embodiments, the pharmaceutical formulation containing such amount of L-ornithine phenylacetate is in two or more unit dosage forms. For example, some embodiments comprise administering 1 to 5 unit dosage forms each comprising from about 0.1 g to about 2 g of L-ornithine phenylacetate, or about 2 to 4 unit dosage forms each comprising from about 0.5 g to about 1.25 g of L-ornithine phenylacetate. Some embodiments comprise administering 4 unit dosage forms each comprising about 1.25 g of L-ornithine phenylacetate. Some embodiments comprise administering 5 unit dosage forms each comprising about 1 g of L-ornithine phenylacetate. Some other embodiments comprise administering 1 unit dosage form comprising about 5 g of L-ornithine phenylacetate. In one embodiment, the pharmaceutical formulation is administered three times a day. For example, where multiple unit dosage forms are administered at a time, the multiple unit dosage administration is repeated three time a day. In another embodiment, the pharmaceutical formulation is administered once a day.

In some embodiments of the methods described herein, the pharmaceutical formulation provides conversion of phenylacetate to phenylacetylglutamine over 24 hours of greater than about 30%, greater than about 40%, greater than about 50%, greater than about 60%, greater than about 70%, greater than about 80%, or greater than about 90%. In some further embodiments, the pharmaceutical formulation provides conversion of phenylacetate to phenylacetylglutamine over 24 hours of greater than about 80%. In some embodiments, the conversion efficiency is determined based on excreted urinary phenylacetylglutamine.

In some embodiments of the methods described herein, the pharmaceutical formulation provides conversion of phenylacetate to phenylacetylglutamine over 12 hours of greater than about 30%, greater than about 40%, greater than about 50%, greater than about 60%, greater than about 70%, greater than about 80%, or greater than about 90%. In some further embodiments, the formulation provides conversion of phenylacetate to phenylacetylglutamine over 12 hours of greater than about 60%. In some embodiments, the conversion efficiency is determined based on excreted urinary phenylacetylglutamine.

In any embodiment of the plasma Cmax or AUC value described herein, such value may be selected from a mean or median plasma Cmax or AUC value. In some embodiments, the plasma Cmax and AUC described herein is achieved after a single dose administration of an oral pharmaceutical formulation of L-ornithine phenylacetate. In some other embodiments, the plasma Cmax and AUC described herein is a stead-state plasma Cmax and AUC achieved after mutiple doses administration of an oral pharmaceutical formulation of L-ornithine phenylacetate. In some embodiments, the plasma Cmax and AUC described herein are measured at fasting state. In some other embodiments, these PK parameters are measured at fed state.

Some examples of substances that can serve as pharmaceutically-acceptable carriers or excipients thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

In some embodiments, the oral dosage form of L-ornithine phenylacetate may be in the form of a liquid, in particular a liquid solution. The oral dosage formulation may also comprise conventional pharmaceutical compatible adjuvants, excipients or carriers, including those commonly used in the oral solution formulation as discussed herein.

In some embodiments, the oral formulation described herein provides for lower doses than previously expected. For example, RAVICTI® (glycerol phenylbutyrate, a pre-prodrug of phenylacetate) was found in clinical studies at a dose of 6 mL (delivering about 1.02 g/mL of phenylbutyrate) twice daily to lower the incidence of hepatic encephalopathy events. Both the immediate release and the controlled release oral pharmaceutical formulations of L-ornithine phenylacetate described herein provide similar percentage of PAGN urinary excretion, permitting use of substantially lower API doses, compared to RAVICTI® or other phenylacetate formulations.

EXAMPLES

The following examples, including experiments and results achieved, are provided for illustrative purposes only and are not to be construed as limiting the present application.

Example 1—Phase I Pharmacokinetic Studies in Healthy Humans

An open-label, five-treatment, five-period single-dose crossover Phase 1 human clinical study was conducted to evaluate the pharmacokinetics of phenylacetic acid and phenylacetylglutamine after a single dose of three extended-release oral dosage forms of L-ornithine phenylacetate in comparison to RAVICTI® (glycerol phenylbutyrate), a prodrug of phenylacetic acid. The study also compared the pharmacokinetics and safety of single doses of the three extended-release oral dosage forms of L-ornithine phenylacetate in comparison to a single dose of an immediate release oral solution of L-ornithine phenylacetate.

The five treatments are listed as follows: each of Treatment A, B, and C refers to a single oral dose of 10 g Formulations A, B and C (each is an equivalent of about 5 g PAA) and the components of these formulations are summarized in Table 1 below; Treatment D refers to a single oral dose of 6 mL RAVICTI® (equivalent of about 5 g PAA); Treatment E refers to a single oral dose of an immediate release formulation of 5 g L-ornithine phenylacetate (equivalent of about 2.5 g PAA).

TABLE 1

| Component | Quantity (g/dose) | | |
| --- | --- | --- | --- |
| | Formulation A | Formulation B | Formulation C |
| Drug Layered Core Pellets (g) | | | |
| L-ornithine phenylacetate | 10.00 | 10.00 | 10.00 |
| Sugar Spheres (500-600 µm) | 17.57 | 17.57 | 17.57 |
| Talc | 0.50 | 0.50 | 0.50 |
| Hydroxypropylmethylcellulose | 0.50 | 0.50 | 0.50 |
| Total (Dry weight) Core Pellets | 28.57 | 28.57 | 28.57 |
| Extended Release Coating (g) | | | |
| Ethyl cellulose | 4.54 | 11.02 | NA |
| Dibutyl Sebacate | 0.50 | 1.22 | NA |
| Eudragit NM 30D | NA | NA | 11.42 |
| Talc | NA | NA | 8.57 |
| Total Dry Weight per Unit Dose | 33.6 | 40.8 | 48.6 |

The primary objective is to assess the plasma profiles and pharmacokinetics of phenylacetic acid (a potent ammonia scavenger), ornithine and phenylacetylglutamine (the end-product responsible for clearing ammonia) following a single oral dose of three extended-release formulations of L-ornithine phenylacetate in comparison to an oral solution of L-ornithine phenylacetate and a prodrug of phenylacetic acid (glycerol phenylbutyrate, RAVICTI®) in healthy human subjects. The secondary objective is to determine the safety, tolerability, and palatability of three extended-release formulations in healthy subjects.

Eligible male or female adult healthy subjects were enrolled to first receive four treatments (Treatments A-D) over 4 dosing periods in a crossover fashion using a balanced 4×4 Latin Square design with an at least 7-day washout interval between treatments followed by receiving Treatment E for all subjects in the fifth (last) dose period after a minimum 7-day washout interval. Following dosing in each dose period, subjects underwent serial blood and urine sampling up to 24 hrs post dose for PK assessment.

PK Assessments

In the dose periods where Treatment A, B, C, or D was administered (the ER formulations of L-ornithine phenylacetate or RAVICTI®), venous blood samples (5 mL each) were collected at the following time points: immediately (within 15 mins) prior to dosing, and then at 0.5, 1, 1.5, 2, 2.5, 3, 3.5, 4, 5, 6, 8, 10, 12, 16, 20, and 24 hrs post dose. In the dose period where the immediate release formulation of L-ornithine phenylacetate was administered (Period 5), venous blood samples (5 mL each) were collected at the following time points: immediately (within 15 mins) prior to dosing, and then at 0.25, 0.5, 0.75, 1, 1.5, 2, 2.5, 3, 3.5, 4, 4.5, 5, 6, 7, 8, 10, and 12 hrs post-dose.

In addition, urine samples were collected at the following time intervals: within 1 hour prior to dosing (spot sample), and then cumulatively over the intervals of 0-4, 4-8, 8-12, and 12-24 hrs post dose. Plasma samples were separated by centrifugation within 1 hour of blood collection and stored at approximately −80° C. until analyzed. The total urine volume for each collection interval were measured and recorded and aliquots of urine were stored at approximately −80° C. until analyzed.

Bioanalytical Methods

Plasma samples were analyzed for concentrations of phenylacetic acid (PAA), phenylacetylglutamine (PAGN) and ornithine (ORN) using a validated LC-MS/MS method. All urine samples were analyzed for concentrations of PAGN using a validated LC-MS/MS method.

Endpoints

Pharmacokinetics: Plasma concentration vs. time profiles of phenylacetate, ornithine, and phenylacetylglutamine following a single oral dose of each of the study drug were analyzed by noncompartmental PK methods. Pharmacokinetic parameters that were determined include $C_{max}$, $t_{max}$, $AUC_{0-t}$, $AUC_{0-\infty}$, $C_{12}$ and $t_{1/2}$. The amount of PAGN excreted in urine and the percent of PAA dose excreted in urine as PAGN over each collection interval and the entire 24 hr interval were also determined.

Figure 2:
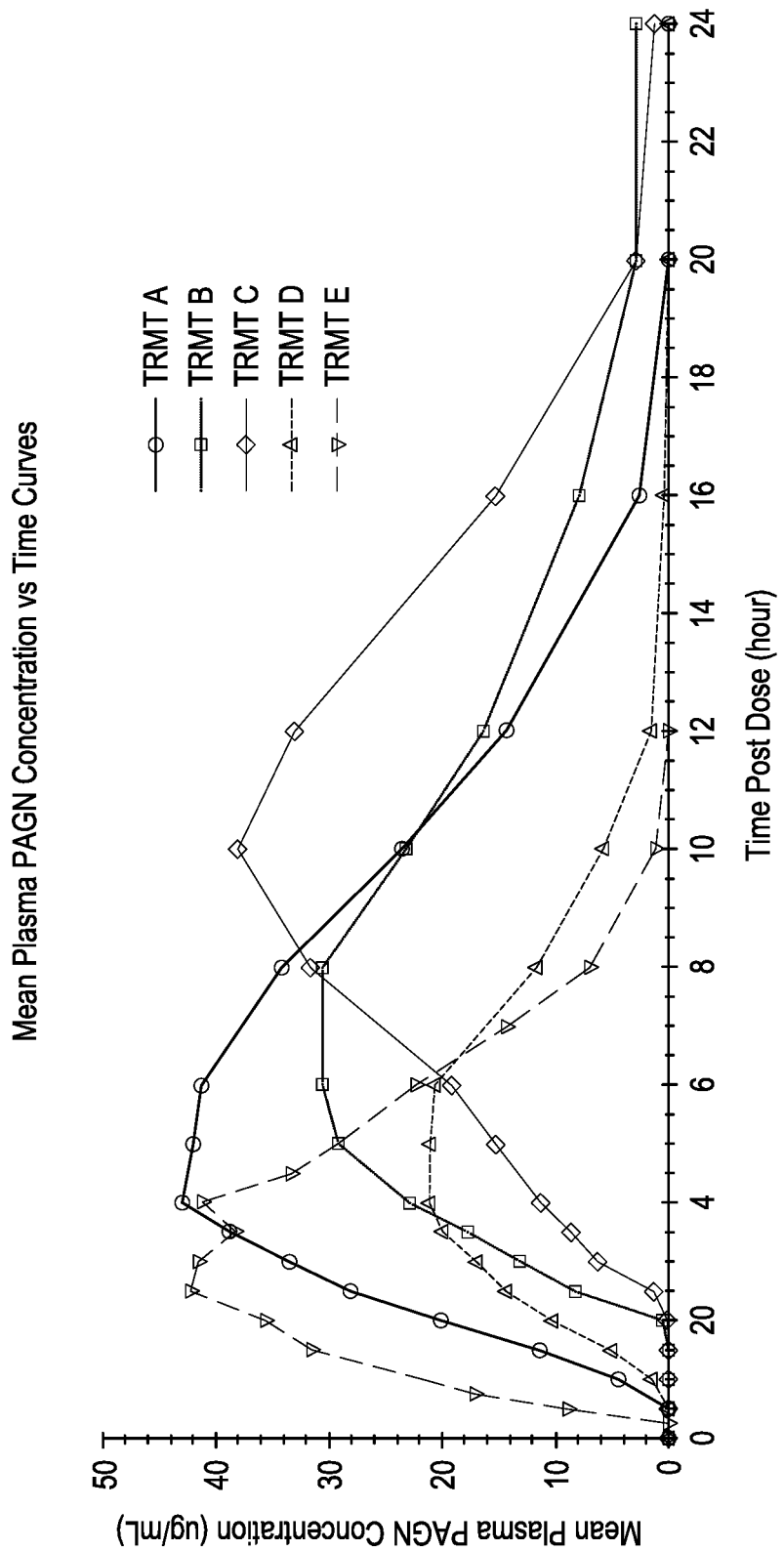
FIG. 2 is a line chart depicting the in vivo surrogate plasma pharmacodynamic profiles of phenylacetylglutamine (PAGN) in humans after administration of controlled-release Formulations A, B, and C, RAVICTI®, and an immediate-release oral formulation of L-ornithine phenylacetate.

FIG. 1 and FIG. 2 illustrate the mean plasma profiles of PAA and PAGN, respectively, from this Phase 1 study. FIG. 1 demonstrates the Mean Plasma PAA concentration vs. time curves following administration of a single oral dose of the controlled-release formulations in comparison to the immediate-release solution and glycerol phenylbutyrate. FIG. 2 demonstrates the Mean Plasma PAGN concentration vs. time curves following administration of a single oral dose of the controlled-release formulations in comparison to the immediate-release solution and glycerol phenylbutyrate.

The mean maximum concentration (Cmax) of plasma PAA from three extended-release formulations ranged from approximately 50 to 90 µg/mL occurring at various time points over 4 to 9 hours after dosing. For comparison, RAVICTI® produced a mean plasma PAA Cmax of approximately 10 µg/mL at 4 to 6 hours after dosing. The plasma PAA data after a single oral dose of 6 mL RAVICTI® are consistent with published data in healthy subjects. In addition, PAA exposure with the extended-release formulations of L-ornithine phenylacetate showed lower inter-subject variability than RAVICTI®.

Plasma profiles of PAGN, the end-product of ammonia scavenging, also demonstrated a similar pattern as the PAA profiles. The mean Cmax of plasma PAGN from the three extended-release formulations of L-ornithine phenylacetate ranged from approximately 30 to 45 µg/mL occurring at various time points over 4 to 10 hours after dosing. For comparison, RAVICTI® produced a mean plasma PAGN Cmax of about 20 to 25 µg/mL at approximately 5 hours. These data are also consistent with the published data in healthy subjects.

The total urinary excretion data of PAGN over 24 hours is summarized in Table 2 below. The mean PAGN excretion amount was comparable for Treatment A through C, each with about 80% PAA converted to PAGN excretion over 24 hours. In contrast, Treatment D with RAVICTI® only showed about 40% conversion efficiency compared to Treatment A through C at approximately the same molar PAA dose (in the case of RAVICTI®, PAA is provided from the glycerol phenylbutyrate prodrug). It was surprisingly observed that the immediate release formulation Treatment E also exhibited about 80% conversion efficiency, which provided a similar mean PAGN excretion amount at approximately half the molar dose of PAA administered in the RAVICTI® arm.

TABLE 2

| Treatment | Statistics | Total PAGN Amount Excreted over 24 hours (G) | PAA Equivalents Excreted over 24 hours (G) | Percent PAA Dose Excreted over 24 hours (%) |
|---|---|---|---|---|
| A | N | 12 | 12 | 12 |
|   | Mean | 8.26 | 4.26 | 83.8 |
|   | Median | 8.47 | 4.37 | 86.0 |
|   | % CV | 14.7 | 14.7 | 14.7 |
| B | N | 12 | 12 | 12 |
|   | Mean | 7.77 | 4.00 | 78.9 |
|   | Median | 7.77 | 4.00 | 78.8 |
|   | % CV | 10.7 | 10.7 | 10.8 |
| C | N | 12 | 12 | 12 |
|   | Mean | 8.53 | 4.39 | 86.6 |
|   | Median | 8.39 | 4.33 | 85.3 |
|   | % CV | 11.3 | 11.3 | 11.3 |
| D | N | 12 | 12 | 14 |
|   | Mean | 4.11 | 212 | 42.7 |
|   | Median | 4.06 | 2.09 | 42.1 |
|   | % CV | 24.9 | 24.9 | 24.9 |
| E | N | 12 | 12 | 12 |
|   | Mean | 4.01 | 2.07 | 81.5 |
|   | Median | 4.14 | 2.13 | 84.0 |
|   | % CV | 15.2 | 15.1 | 15.1 |

Conclusion: The controlled-release and immediate release formulations were well tolerated throughout the study, with no toxicities or serious adverse events observed. The results showed a robust, extended-release pattern for all three extended-release formulations with mean plasma PAA concentrations exceeding those achieved with RAVICTI® (glycerol phenylbutyrate) at all time points for at least 24 hours post dose. In addition, mean plasma PAGN concentrations and urinary PAGN excretion were greater for all three extended-release dosage forms than for RAVICTI® at approximately the same molar PAA dose. It also demonstrated that urinary PAGN excretion for the immediate release formulation of L-ornithine phenylacetate was approximately twice as efficient as for RAVICTI®.

Example 2—Phase I Pharmacokinetic Studies in Child-Pugh Class A Subjects

In this example, a single-dose, partially randomized clinical study to evaluate 5 g L-ornithine phenylacetate oral solution administered under fed conditions, fasting conditions, or under fasting conditions following discontinuation of lactulose in 5 subjects with cirrhosis (Child-Pugh class A). The purpose is to determine the pharmacokinetics of PAA and PAGN following a single 5 g dose of L-ornithine phenylacetate oral solution administered under fed conditions, fasting conditions, or under fasting conditions following discontinuation of lactulose as compared to a single 5 g intravenous dose of L-ornithine phenylacetate under fasting conditions in subjects with cirrhosis (Child-Pugh class A).

The treatments are summarized as follows: Treatment A is a single 5 g oral dose of L-ornithine phenylacetate oral solution administered under fasting conditions; Treatment B is a single 5 g oral dose of L-ornithine phenylacetate oral solution administered under fed conditions; Treatment C is a single 5 g intravenous dose of L-ornithine phenylacetate solution infused over 1 hour under fasting conditions; and Treatment D is a single 5 g oral dose of L-ornithine phenylacetate oral solution administered under fasting condition following discontinuation of lactulose.

Eligible subjects received a single dose of study drug on Day 1. Subjects were confined at the Phase 1 unit from admission on Day −1 until the final blood sample for pharmacokinetic assessment is obtained. In Dosing Period 1, all subjects received intravenous L-ornithine phenylacetate (Treatment C), and in Dosing Period 4, all subjects received a single dose of L-ornithine phenylacetate oral solution following discontinuation of lactulose (Treatment D). Treatments A and B were administered during Dosing Periods 2 and 3 in a randomized fashion. At the end of Dosing Periods 1, 2, and 3, subjects returned to the clinic for the next dosing period. At the end of Dosing Period 3, all subjects discontinued lactulose. There was a minimum 4-day washout interval between consecutive dosing periods.

Pharmacokinetic Assessments

Following each oral dose (Treatments A, B, and D), venous blood samples (5 mL each) was collected at the following time points: immediately (within 15 minutes) prior to dosing, and then at 0.25, 0.5, 0.75, 1, 1.5, 2, 2.5, 3, 3.5, 4, 5, 6, 7, 8, 10, and 12 hours post-dose. For Treatment D (Dosing Period 4), an additional blood sample was obtained at 24 hours post-dose. Following the intravenous dose (Treatment C), venous blood samples (5 mL each) were collected at the following time points: immediately (within 15 minutes) prior to the start of infusion, and then at 0.5 hours after the start of infusion, and immediately prior to the end of infusion, subsequently at 10, 20, 30, 45 and 60 minutes after the end of infusion, and then at 1.5, 2, 2.5, 3, 4, 6, 8, 10, 12, and 24 hours after the end of infusion.

In addition, urine samples were collected for each treatment at the following time intervals: within 1 hour prior to dosing (spot sample), and then cumulatively over the intervals of 0-4, 4-8, and 8-12 hours post-dose. For Treatments C and D (Dosing Periods 1 and 4), urine were also collected over the 12-24 hour post-dose interval.

Figure 3:
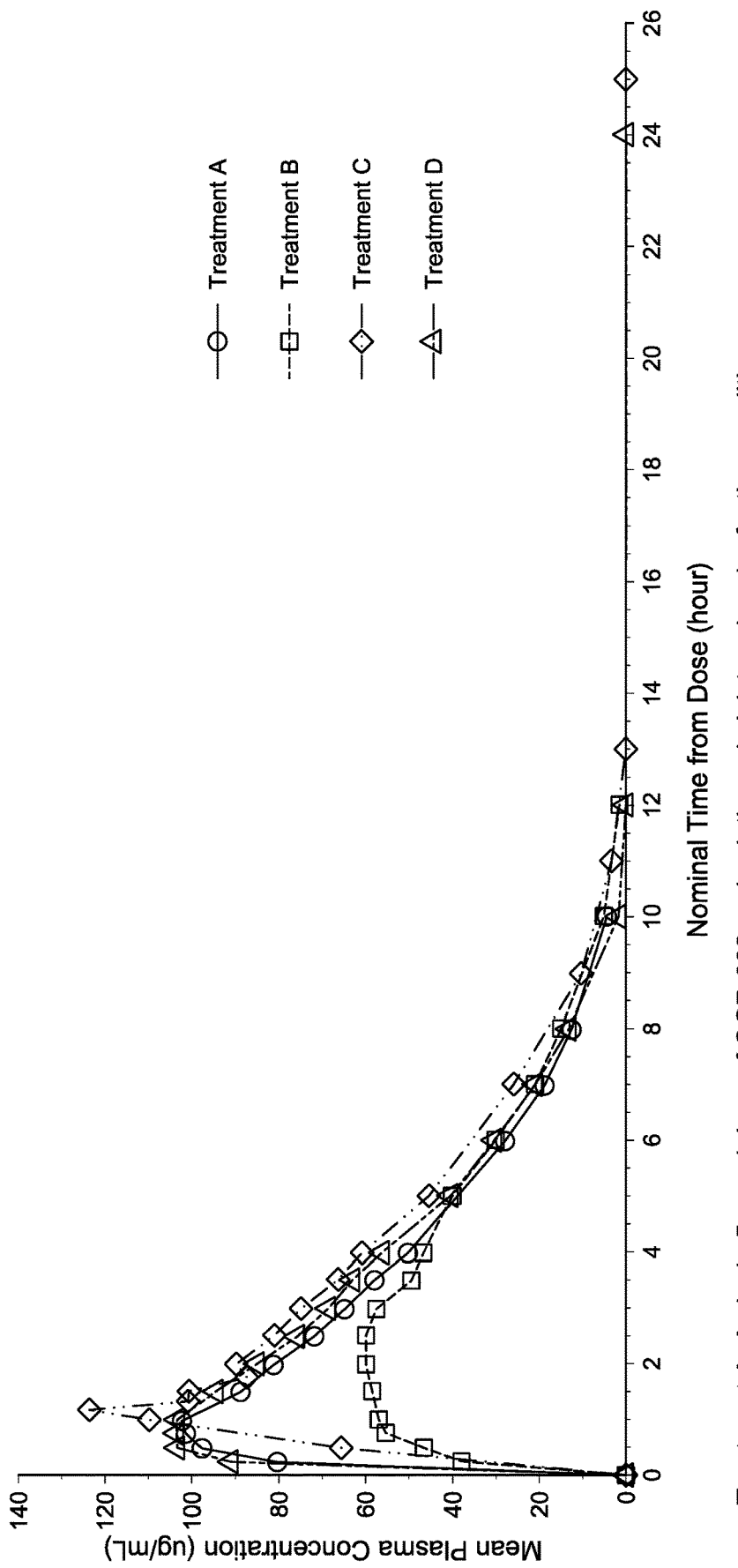
FIG. 3 is a line chart depicting the in vivo plasma pharmacokinetic profiles of phenylacetic acid (PAA) in subjects with chronic liver disease classification Child-Pugh class A after administration of a single dose of 5 g L-ornithine phenylacetate under four different treatments.
Figure 4:
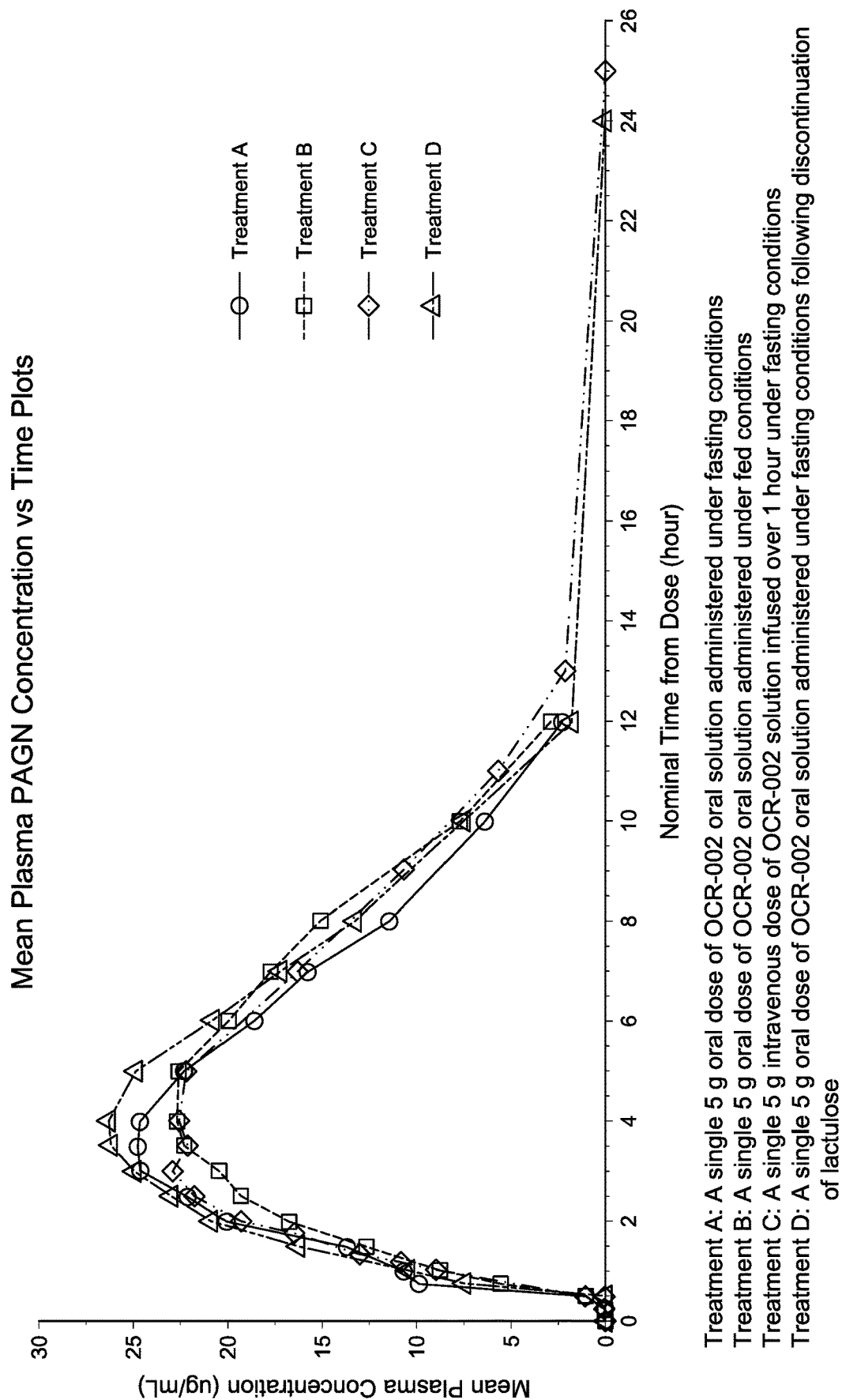
FIG. 4 is a line chart depicting the in vivo surrogate plasma pharmacodynamic profiles of phenylacetylglutamine (PAGN) in subjects with chronic liver disease classification Child-Pugh class A after administration of a single dose of 5 g L-ornithine phenylacetate under four different treatments.

FIG. 3 and FIG. 4 illustrate the mean plasma profiles of PAA and PAGN, respectively, from this Phase 1 study. FIG. 3 demonstrates the Mean Plasma PAA concentration vs. time curves following administration of four treatments (Treatments A, B, C and D) described above. FIG. 4 demonstrates the Mean Plasma PAGN concentration vs. time curves following administration of the four treatments (Treatments A, B, C and D) described above. The pharmacokinetic parameters of PAA and PAGN are summarized in Table 3 and Table 4.

TABLE 3

Summary of Pharmacokinetic Parameter Estimates of PAA

| Treatment | Statistics | $C_{max}$ (μg/mL) | $t_{max}$ (hr) | $t_{1/2}$ (hr) | $AUC_{(0-t)}$ (hr * μg/mL) | $AUC_{(0-inf)}$ (hr * μg/mL) | % $AUC_{ext}$ (%) | F (%)* | CL (L/hr) |
|---|---|---|---|---|---|---|---|---|---|
| C | N | 4 | 4 | 4 | 4 | 4 | 4 | | 4 |
| | Mean | 113 | 1.16 | 1.99 | 473.4 | 514.9 | 8.03 | | 5.97 |
| | Median | 109 | 1.08 | 2.05 | 495.0 | 550.8 | 6.79 | | 4.75 |
| | CV % | 30.3 | 22.0 | 23.9 | 43.6 | 42.4 | 48.5 | | 56.7 |
| A | N | 5 | 5 | 5 | 5 | 5 | 5 | 4 | |
| | Mean | 105 | 0.82 | 1.38 | 439.6 | 453.2 | 3.43 | 96.0 | |
| | Median | 115 | 0.80 | 1.29 | 431.4 | 446.5 | 3.38 | 96.2 | |
| | CV % | 27.6 | 25.4 | 14.9 | 47.6 | 46.6 | 39.6 | 3.64 | |
| B | N | 5 | 5 | 5 | 5 | 5 | 5 | 4 | |
| | Mean | 66.7 | 1.55 | 1.36 | 360.1 | 373.7 | 4.15 | 80.4 | |
| | Median | 66.2 | 1.00 | 1.31 | 347.7 | 363.3 | 4.20 | 81.8 | |
| | CV % | 21.0 | 71.7 | 12.9 | 43.4 | 42.1 | 42.5 | 7.4 | |
| D | N | 5 | 5 | 5 | 5 | 5 | 5 | 4 | |
| | Mean | 113 | 0.66 | 1.53 | 457.9 | 483.0 | 4.90 | 103.0 | |
| | Median | 113 | 0.77 | 1.49 | 515.0 | 557.9 | 4.69 | 99.2 | |
| | CV % | 23.4 | 59.9 | 16.8 | 35.7 | 36.4 | 35.7 | 13.9 | |

TABLE 4

Summary of Pharmacokinetic Parameter Estimates of PAGN

| Treatment | Statistics | $C_{max}$ (μg/mL) | $t_{max}$ (hr) | $t_{1/2}$ (hr) | $AUC_{(0-t)}$ (hr * μg/mL) | $AUC_{(0-inf)}$ (hr * μg/mL) | % $AUC_{ext}$ (%) | PAGN/PAA Molar $AUC_{(0-inf)}$ Ratio |
|---|---|---|---|---|---|---|---|---|
| C | N | 4 | 4 | 4 | 4 | 4 | 4 | 4 |
| | Mean | 24.0 | 3.65 | 2.58 | 166.5 | 198.7 | 16.83 | 0.224 |
| | Median | 24.3 | 3.51 | 2.49 | 158.7 | 185.4 | 14.92 | 0.207 |
| | CV % | 6.8 | 30.9 | 14.3 | 28.7 | 24.9 | 30.1 | 38.3 |
| A | N | 5 | 5 | 5 | 5 | 5 | 5 | 5 |
| | Mean | 26.0 | 4.02 | 2.85 | 161.1 | 199.5 | 18.76 | 0.256 |
| | Median | 24.4 | 4.02 | 2.81 | 168.4 | 208.5 | 19.31 | 0.235 |
| | CV % | 19.7 | 25.2 | 40.0 | 28.5 | 30.9 | 41.4 | 38.6 |
| B | N | 5 | 5 | 5 | 5 | 5 | 5 | 5 |
| | Mean | 23.9 | 4.42 | 2.78 | 162.0 | 203.8 | 19.87 | 0.304 |
| | Median | 23.7 | 4.00 | 3.01 | 162.0 | 210.4 | 23.01 | 0.288 |
| | CV % | 16.5 | 19.1 | 32.8 | 32.4 | 34.0 | 42.2 | 36.8 |
| D | N | 5 | 5 | 5 | 5 | 5 | 5 | 5 |
| | Mean | 27.4 | 3.93 | 2.60 | 177.1 | 205.9 | 14.00 | 0.237 |
| | Median | 26.1 | 4.03 | 2.70 | 172.8 | 214.3 | 13.76 | 0.247 |
| | CV % | 24.5 | 19.0 | 29.0 | 32.0 | 31.4 | 31.6 | 36.7 |

The plasma exposure data and PK parameter estimates of PAA in Child-Pugh A subjects after a single oral dose of 5 g of L-ornithine phenylacetate were as expected based on projections from previous data in healthy subjects.

Based on a small number of subjects, the study showed that after a single oral dose of 5 g of L-ornithine phenylacetate to Child-Pugh A subjects, mean peak plasma PAA concentration (Cmax) was slight (20%) lower and overall plasma exposure to PAA ($AUC_{0-inf}$) was about 30% higher than that in healthy subjects. The slightly higher AUC value in Child-Pugh A subjects is most likely due to slower metabolism of PAA in Child-Pugh A subjects and longer elimination half life of PAA which increased from about 0.9 hr in healthy subjects to 1.4 hr in Child-Pugh A subjects. There was large intersubject variability in plasma PAA exposure after either intravenous or oral administration of L-ornithine phenylacetate.

After an oral dose of L-ornithine phenylacetate, PAA was almost completely bioavailable, as shown by the absolute bioavailability value (F) of 96% for PAA, determined in Child-Pugh A subjects after a single 5 g oral dose of L-ornithine phenylacetate in comparison to an intravenous dose.

Subjects on lactulose appeared to have similar PAA and PAGN plasma profiles and pharmacokinetics from administration of a single oral dose of L-ornithine phenylacetate before and after lactulose has been washed out.

Plasma exposure and pharmacokinetic profiles of PAGN were comparable between the four treatments, i.e., after a single oral dose of 5 g L-ornithine phenylacetate intravenously or orally with or without food or without lactulose in Child-Pugh A subjects. Mean $AUC_{0-inf}$ of PAGN was slightly (~10%) lower in Child-Pugh A subjects than in healthy subjects. Mean plasma half life of PAGN in Child-Pugh subjects, 2.6 hrs, was longer than that in healthy subjects, 1.4 hours.

TABLE 5

Summary of Urinary Excretion Data of PAGN

| Treatment | Statistics | Duration of Urine Collection Interval | Total PAGN Amount Excreted (G) | Total PAA Equivalents Excreted (G) | Percent PAA Dose Excreted (%) |
|---|---|---|---|---|---|
| C | N | 24 hour | 4 | 4 | 4 |
|   | Mean |  | 3.86 | 1.99 | 78.3 |
|   | Median |  | 3.91 | 2.02 | 79.4 |
|   | CV % |  | 22.9 | 23.1 | 23.1 |
| A | N | 12 hour | 5 | 5 | 5 |
|   | Mean |  | 3.31 | 1.70 | 67.1 |
|   | Median |  | 3.16 | 1.63 | 64.2 |
|   | CV % |  | 22.3 | 22.2 | 22.2 |
| B | N | 12 hour | 5 | 5 | 5 |
|   | Mean |  | 3.45 | 1.78 | 70.0 |
|   | Median |  | 3.36 | 1.73 | 68.2 |
|   | CV % |  | 19.0 | 19.0 | 19.0 |
| D | N | 24 hour | 5 | 5 | 5 |
|   | Mean |  | 4.17 | 2.15 | 84.7 |
|   | Median |  | 4.02 | 2.07 | 81.6 |
|   | CV % |  | 14.9 | 14.8 | 14.8 |

Urinary excretion data showed that the mean percent PAA dose recovered in urine as PAGN was 78.3% after a single IV dose of L-ornithine phenylacetate, and 84.7% after a single oral dose of L-ornithine phenylacetate (Treatment D). The lower % PAA dose recovered in urine as PAGN in Treatments A and B could be due to the shorter urine collection interval, i.e., 12 hours.

What is claimed is:

1. A method for treating or ameliorating hyperammonemia, comprising orally administering to a subject in need thereof an immediate release pharmaceutical formulation comprising L-ornithine phenylacetate in a daily oral dosage of about 8 g to about 12 g.

2. The method of claim 1, wherein the subject has liver cirrhosis with a classification of Child-Pugh class A, B or C.

3. The method of claim 1, wherein the subject has one or more conditions selected from the group consisting of hepatic encephalopathy, portal hypertension, and urea cycle disorder.

4. The method of claim 1, comprising orally administering 2 to 5 unit dosage forms each comprising from about 0.5 g to about 2 g L-ornithine phenylacetate two or three times a day.

5. The method of claim 1, wherein the immediate release pharmaceutical formulation comprising L-ornithine phenylacetate is administered in a daily dosage of about 8 g to about 10 g.

6. The method of claim 5, wherein the immediate release pharmaceutical formulation is administered two times a day, each time administering about 4 g to about 5 g L-ornithine phenylacetate.

7. The method of claim 6, wherein each time the immediate release pharmaceutical formulation is administered in 4 unit dosage forms each comprising about 1 g of L-ornithine phenylacetate.

8. The method of claim 1, wherein the immediate release pharmaceutical formulation is administered two times a day, each time administering about 4 g to about 6 g L-ornithine phenylacetate.

9. A method for treating or ameliorating hyperammonemia, comprising orally administering to a subject in need thereof an immediate release pharmaceutical formulation comprising L-ornithine phenylacetate in a daily dosage of about 8 g to about 12 g, wherein said administration provides a plasma Cmax of phenylacetic acid ranging from about 10 µg/mL to about 150 µg/mL.

10. The method of claim 9, wherein the administration provides a plasma Cmax of phenylacetylglutamine ranging from about 5 µg/mL to about 100 µg/mL.

11. The method of claim 9, wherein the subject has liver cirrhosis with a classification of Child-Pugh class A, B or C.

12. The method of claim 9, wherein the subject has one or more conditions selected from the group consisting of hepatic encephalopathy, portal hypertension, and urea cycle disorder.

13. The method of claim 9, comprising orally administering 2 to 5 unit dosage forms each comprising from about 0.5 g to about 2 g of L-ornithine phenylacetate two or three times a day.

14. The method of claim 9, wherein the immediate release pharmaceutical formulation comprising L-ornithine phenylacetate is administered in a daily dosage of about 8 g to about 10 g.

15. The method of claim 14, wherein the immediate release pharmaceutical formulation is administered two times a day, each time administering about 4 g to about 5 g L-ornithine phenylacetate.

16. The method of claim 15, wherein each time the immediate release pharmaceutical formulation is administered in 4 unit dosage forms each comprising about 1 g of L-ornithine phenylacetate.

17. The method of claim 9, wherein the immediate release pharmaceutical formulation is administered two times a day, each time administering about 4 g to about 6 g L-ornithine phenylacetate.

18. A method for treating or ameliorating hyperammonemia, comprising orally administering to a subject in need thereof an immediate release pharmaceutical formulation comprising L-ornithine phenylacetate in a daily dosage of about 8 g to about 12 g, wherein said administration provides a plasma $AUC_{0-t}$ or $AUC_{0-inf}$ of phenylacetic acid ranging from about 100 hr*µg/mL to about 1000 hr*µg/mL.

19. The method of claim 18, wherein the plasma $AUC_{0-t}$ or $AUC_{0-inf}$ of phenylacetic acid is from about 400 hr*µg/mL to about 550 hr*µg/mL.

20. The method of claim 18, wherein the plasma $AUC_{0-t}$ or $AUC_{0-inf}$ of phenylacetylglutamine is from about 25 hr*µg/mL to about 500 hr*µg/mL.

21. The method of claim 20, wherein the plasma $AUC_{0-t}$ of phenylacetylglutamine is from about 120 hr*µg/mL to about 180 hr*µg/mL and wherein the plasma $AUC_{0-inf}$ of phenylacetylglutamine is from about 100 hr*µg/mL to about 250 hr*µg/mL.

22. The method of claim 18, wherein the subject has liver cirrhosis with a classification of Child-Pugh class A, B or C.

23. The method of claim 18, wherein the subject has one or more conditions selected from the group consisting of hepatic encephalopathy, portal hypertension, and urea cycle disorder.

24. The method of claim 18, comprising orally administering 2 to 5 unit dosage forms each comprising from about 0.5 g to about 2 g of L-ornithine phenylacetate two or three times a day.

25. The method of claim 18, wherein the immediate release pharmaceutical formulation comprising L-ornithine phenylacetate is administered in a daily dosage of about 8 g to about 10 g.

26. The method of claim 25, wherein the immediate release pharmaceutical formulation is administered two times a day, each time administering about 4 g to about 5 g L-ornithine phenylacetate.

27. The method of claim 26, wherein each time the immediate release pharmaceutical formulation is administered in 4 unit dosage forms each comprising about 1 g of L-ornithine phenylacetate.

28. The method of claim 18, wherein the immediate release pharmaceutical formulation is administered two times a day, each time administering about 4 g to about 6 g L-ornithine phenylacetate.

* * * * *